United States Patent
Landis et al.

(10) Patent No.: US 9,095,672 B2
(45) Date of Patent: Aug. 4, 2015

(54) DEVICE FOR SECURING A BREATHING TUBE

(71) Applicant: Airways Development LLC, Kenilworth, NJ (US)

(72) Inventors: Robert M Landis, Mountainside, NJ (US); Wayne W Disanza, Toms River, NJ (US)

(73) Assignee: Airways Development LLC, Kenilworth, NJ (US)

( * ) Notice: Subject to any disclaimer, the term of this patent is extended or adjusted under 35 U.S.C. 154(b) by 391 days.

(21) Appl. No.: 13/688,492

(22) Filed: Nov. 29, 2012

(65) Prior Publication Data

US 2013/0139825 A1 Jun. 6, 2013

Related U.S. Application Data

(60) Provisional application No. 61/567,193, filed on Dec. 6, 2011.

(51) Int. Cl.
*A61M 16/04* (2006.01)
*A61M 25/02* (2006.01)
(Continued)

(52) U.S. Cl.
CPC ....... *A61M 16/0488* (2013.01); *A61M 16/0875* (2013.01); *A44B 18/0084* (2013.01);
(Continued)

(58) Field of Classification Search
CPC . A61M 25/02; A61M 16/0488; A61M 16/04; A61M 16/0497; A61M 16/00; A61M 16/0493; A61M 16/0875; A61M 16/0447; A61M 16/0683; A62B 9/06; A41F 1/002; A42B 3/04; A42B 3/08; A44B 18/00; A44B 18/0049; A44B 18/0084; A45C 13/1069; A45D 8/00; A45D 8/34; A45F 3/00; A45F 3/14; A45F 5/00; A45F 5/10; A45F 5/1026; A61F 13/00021; A61F 13/00063; A61F 13/04; A61F 13/041; A61F 13/06; A61F 13/064; A61F 13/068; A61F 13/10; A61F 13/104; A61F 13/107; A61F 13/12; A61N 1/044; A61N 1/0472; A63C 11/00; A63C 11/02; A63C 11/021; A63C 11/025; B29C 43/222; B29C 43/46; B32B 3/02; B32B 3/06; B32B 37/00; B62J 6/00; B65D 33/14; B65D 33/1658; B65D 63/10; B65D 63/1018; B65D 63/1027; B65D 63/1063; B65D 63/14; B65D 77/10; B65D 77/18; F16L 3/12; F16L 3/137; F21L 15/14
USPC ............ 128/200.24, 200.26, 206.21, 206.27, 128/207.11, 207.13, 207.14, 207.17, 128/207.18, DIG. 26, 207.15, 882, 911, 128/912, DIG. 14, DIG. 15, DIG. 24; 604/174, 179, 180; 224/901.4, 901.6, 224/901.8; 24/16 R See application file for complete search history.

(56) References Cited

U.S. PATENT DOCUMENTS 3,422,817 A 1/1969 Mishkin et al.
3,585,997 A 6/1971 Ancerewicz, Jr.
(Continued)

FOREIGN PATENT DOCUMENTS

EP 0145142 A1 * 9/1984

*Primary Examiner* — Annette Dixon
(74) *Attorney, Agent, or Firm* — Carter DeLuca Farrell & Schmidt LLP

(57) ABSTRACT

A device for securing a tube in position includes a strip of material and first, second, and third attachment members. The strip of material defines a first surface and a second, opposed surface. The strip of material further includes first and second end portions, and an intermediate portion. The first and second attachment members are disposed on the first surface of the strip of material and positioned adjacent the respective first and second end portions. The third attachment member is disposed on the second surface of the strip of material and is positioned adjacent the intermediate portion. The strip of material is configured to wrap around a tube with the first, second, and third attachment members releasably engaging a strap member to secure the tube in position.

18 Claims, 1 Drawing Sheet

(51) Int. Cl.
  *A44B 18/00* (2006.01)
  *A61M 16/08* (2006.01)
  *A61M 16/06* (2006.01)

(52) U.S. Cl.
  CPC ........ *A61M16/0497* (2013.01); *A61M 16/0683* (2013.01); *A61M 25/02* (2013.01); *A61M 2209/088* (2013.01)

(56) References Cited

U.S. PATENT DOCUMENTS

| | | | |
|---|---|---|---|
| 3,834,380 A * | 9/1974 | Boyd | 604/180 |
| 3,878,849 A * | 4/1975 | Muller et al. | 604/179 |
| 4,088,136 A * | 5/1978 | Hasslinger et al. | 604/179 |
| 4,445,894 A * | 5/1984 | Kovacs | 604/179 |
| 4,569,348 A * | 2/1986 | Hasslinger | 604/179 |
| 4,571,245 A * | 2/1986 | Hubbard et al. | 604/179 |
| 5,000,741 A | 3/1991 | Kalt | |
| 5,038,778 A * | 8/1991 | Lott | 128/207.17 |
| 5,058,579 A | 10/1991 | Terry et al. | |
| 5,292,312 A * | 3/1994 | Delk et al. | 604/180 |
| 5,411,484 A * | 5/1995 | Shattuck | 604/179 |
| 5,692,268 A * | 12/1997 | Case | 24/16 PB |
| 5,879,335 A * | 3/1999 | Martinez et al. | 604/179 |
| 5,918,599 A | 7/1999 | Shesol | |
| 2007/0235034 A1 * | 10/2007 | Weaver | 128/207.18 |
| 2009/0126740 A1 | 5/2009 | Loescher | |

* cited by examiner

DEVICE FOR SECURING A BREATHING TUBE

CROSS-REFERENCE TO RELATED APPLICATIONS

This application claims the benefit of, and priority to, U.S. Provisional Patent Application No. 61/567,193, filed on Dec. 6, 2011, the entire contents of which are hereby incorporated by reference herein.

BACKGROUND

1. Technical Field

The present disclosure relates to devices for securing tubes and, more particularly, to devices for securing a tube, e.g., a breathing tube, to a patient, e.g., to an infant's head.

2. Description of Related Art

Devices and methods of securing medical tubes to patients for receiving fluids and/or for the treatment of diseases are known. The most common method is the use of adhesive tape to secure tubing to the patient. However, there are situations where applying tape to a patient's skin is not desirable and a tapeless method is preferable. There are many known devices that utilize straps with hook/loop fasteners to secure tubing to a patient.

One area of particular interest is the securement of breathing tubes to a newborn infant's head. Typically, straps are wrapped around the infant's head such that the tube(s) can be attached to the straps. This "head gear" may also include a knit cap in combination with the straps. Once the "head gear" is fitted onto the infant's head, the supply tubes, e.g., breathing tubes, are attached to the "head gear." This method is preferred as it allows the tubes to move with the infant's head movements. While common practice, these devices and methods are tedious and laborious to attach to an infant's head. In many cases clinicians are devising make shift methods using safety pins and rubber bands to stabilize breathing tubes. With the increasing costs of healthcare and an increasing burden on caregivers to treat more and more patients in a reduced amount of time, these tedious and laborious devices and methods are proving to be too time consuming. Accordingly, there is a need for a more effective, efficient, and ergonomic device for securing a tube to a patient, particularly with respect to the securement of a breathing tube to an infant's head.

SUMMARY

In accordance with the present disclosure, a device for securing a tube in position is provided. The device includes a strip of material and first, second, and third attachment members. The strip of material defines a first surface and a second, opposed surface. The strip of material further includes a first end portion, a second end portion, and an intermediate portion. The first attachment member is disposed on the first surface of the strip of material and is positioned adjacent the first end portion. The second attachment member is disposed on the first surface of the strip of material and is positioned adjacent the second end portion. The third attachment member is disposed on the second surface of the strip of material and positioned is adjacent the intermediate portion. The strip of material is configured to wrap around a tube with the first, second, and third attachment members releasably engaging a strap member to secure a tube in position relative to the strap member.

In embodiments, the strip of material is formed from a foam and/or at least one of a stretchable, flexible, malleable, and elastomeric material.

In embodiments, the first surface of the strip of material defines a tacky anti-slip or sticky configuration to facilitate retention of the tube.

In embodiments, the first, second, and/or third attachment members include an array of hooks configured to releasably engage an array of loops.

In embodiments, the strip of material defines an expanded-dimension portion adjacent at least one of the first, second, and third attachment members.

A system for securing a tube in position provided in accordance with the present disclosure includes a strap member and a device. The strap member is configured to be secured to a patient and defines an outwardly-facing surface. The strap member includes an attachment structure disposed on the outwardly-facing surface. The device may include any or all of the features of the devices described above. The device is configured to wrap around a tube with the attachment structures of the first, second, and third attachment members releasably engaging the attachment structure of the strap member to secure tube in position relative to the strap member.

In embodiments, the strap member is formed from a non-stretchable or low stretch material suitable for wrapping around an infants head. Wrapping a new born infants head to tightly with elastic material is known to cause head molding.

In embodiments, the first, second, and third attachment members of the device each include an array of hooks and the attachment structure of the strap member includes an array of loops configured to releasably engage the arrays of hooks.

In embodiments, the tube is configured for positioning adjacent the intermediate portion of the strip of material with the first end portion wrapped about the tube in a first direction and the second end portion wrapped about the tube in a second direction.

In embodiments, the first attachment member is configured to engage the strap member on a first side of the tube and the second attachment member is configured to engage the strap member on a second, opposite side of the tube.

A method of securing a tube in position is also provided in accordance with the present disclosure. The method includes providing a strap member, providing a device (e.g., a device similar to any of the embodiments described above), attaching the strap member to a patient, engaging the intermediate portion of the device to the strap member, positioning a tube adjacent the first surface of the device at the intermediate portion thereof, wrapping the first end portion of the device about the tube in a first direction, engaging the first end portion of the device to the strap member, wrapping the second end portion of the device about the tube in a second direction, and engaging the second end portion of the device to the strap member.

In embodiments, engaging the intermediate portion of the device to the strap member includes engaging the third attachment member to the strap member, engaging the first end portion of the device to the strap member includes engaging the first attachment member to the strap member, and/or engaging the second end portion of the device to the strap member includes engaging the second attachment member to the strap member.

In embodiments, wrapping the first and second end portions about the tube in opposite directions provides 360 retention of the tube by the device.

In embodiments, attaching the strap member to a patient includes attaching the strap member about an infant's head.

BRIEF DESCRIPTION OF THE DRAWINGS

The present disclosure is described herein with reference to the drawings wherein.

DETAILED DESCRIPTION

Figure 1:
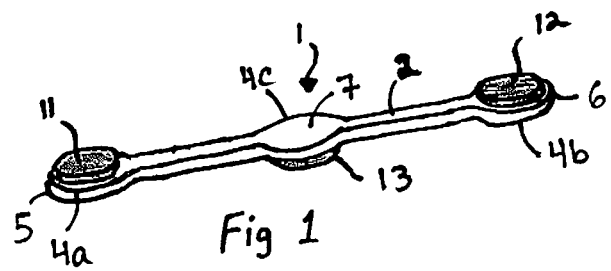
FIG. 1 is a perspective view of a tube securement device provided in accordance with the present disclosure.
Figure 2:
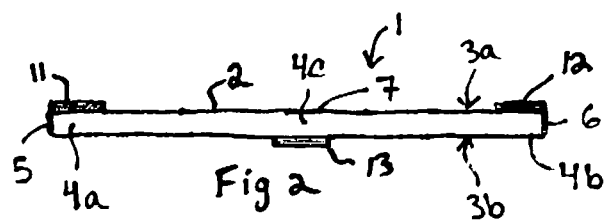
FIG. 2 is a side view of the device of FIG. 1.
Figure 3:
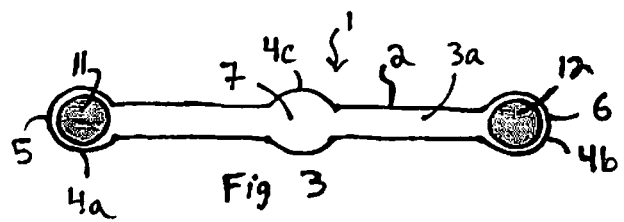
FIG. 3 is a top view of the device of FIG. 1.
Figure 4:
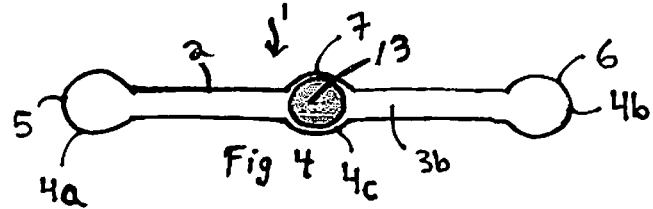
FIG. 4 is a bottom view of the device of FIG. 1.

The present disclosure is described in detail with reference to the drawing figures wherein like reference numerals identify similar or identical elements.

Referring to FIGS. 1-5, a tube securement device provided in accordance with the present disclosure is shown generally identified by reference numeral 1. Device 1 is formed from a strip or length of material 2 having an upper surface 3a, a lower surface 3b, a first end portion 4a, a second end portion 4b, and an intermediate portion 4c. Length of material 2 may be formed from a foam, or other suitable stretchable, flexible, malleable, and/or elastomeric material. Further, length of material 2 may include a tacky anti-slip sticky, or adhesive outer surface to facilitate retention of a tube 14 therebetween (see FIG. 5). That is, length of material 2 may be formed from a tacky anti-slip sticky material, or may be coated with a tacky anti-slip sticky material. It is envisioned that length of material 2 define a length between about 1 and 4 inches and a thickness between about 0.125 inches and 0.25 inches, although other dimensions are also contemplated.

First, second, and third expanded-dimension portions 5, 6, 7, respectively, are defined along the length of material 2 at the first end portion 4a, second end portion 4b, and intermediate portion 4c, respectively, thereof. A first attachment member 11 is disposed on upper surface 3a of device 1 adjacent first expanded-dimension portion 5, a second attachment member 12 is disposed on upper surface 3a of device 1 adjacent second expanded-dimension portion 6, and a third attachment member 13 is disposed on lower surface 3b of device 1 adjacent third expanded-dimension portion 7. First, second, and third attachment members 11, 12, 13, respectively, and first, second, and third expanded-dimension portions 5, 6, 7, respectively, define generally circular or coin-shaped configurations, although other configurations are also contemplated. First, second, and third attachment members 11, 12, 13, respectively, may include any suitable attachment structure, e.g., an array of hooks, for releasably attaching members 11, 12, 13 to a complementary attachment structure, e.g., an array of loops.

Figure 5:
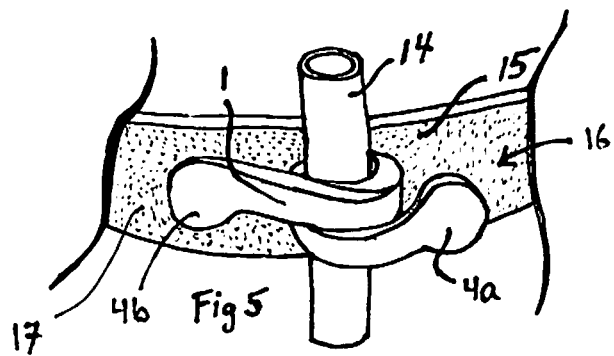
FIG. 5 is a perspective view of the device of FIG. 1 shown securing a tube in position.

With particular reference to FIG. 5, in conjunction with FIGS. 1-4, device 1 is configured for attachment to a strap 15 for securing a tube 14, e.g., a breathing tube, in position relative to a patient, e.g., on an infant's head. Strap 15 defines a generally flat configuration having a first surface 16. First surface 16 includes an attachment structure 17, e.g., an array of loops (or other suitable attachment structure configured to releasably engage attachment members 11, 12, 13), disposed thereon. Attachment structure 17 may substantially cover the entire surface 16, or may only cover portion(s) of surface 16.

In use, strap 15 is initially affixed to the patient. For example, with respect to securing a breathing tube to the head of an infant, strap 15 is secured about the infant's head. Strap 15 is oriented such that first surface 16 thereof is facing outwardly, e.g., away from the patient. Once strap 15 is positioned about the infant's head, device 1 is approximated relative to strap 15 with lower surface 3b of device 1 opposing first surface 16 of strap 15. Thus, upon further approximation and, ultimately, urging of device 1 into strap 15, the hooks (or other attachment structure) of attachment member 13 are engaged with the loops (or other feature) of attachment structure 17, thereby releasably engaging device 1 to strap 15 adjacent intermediate portion 4c. Due to the expanded-dimension portion 7, adjacent which attachment member 13 is disposed, a relatively greater surface area for engagement between the hooks and loops is provided, thus enabling a more secure engagement between device 1 and strap 15.

With attachment member 13 of device 1 secured to strap 15 as detailed above, tube 14 may be positioned adjacent the outwardly-facing upper surface 3a of device, at intermediate portion 4c of device 1. Next, first end portion 4a is bent, or wrapped over tube 14 in a first direction and second end portion 4b is bent, or wrapped over tube 14 in a second, opposite direction, to achieve the configuration shown in FIG. 5. First end portion 4a is then urged into engagement with strap 15 via the engagement of attachment member 11 with attachment structure 17. Likewise, second end portion 4b is then urged into engagement with strap 15 via the engagement of attachment member 12 with attachment structure 17. Similarly as described above, expanded-dimension portions 5 and 6 provide a greater surface area of engagement between first and second end portions 4a, 4b and strap 15, thus facilitating retention.

Once first and second end portions 4a, 4b are secured to strap 15 with tube 14 therebetween, as described above and as shown in FIG. 5, tube 14 is secured in position. In particular, device 1 provides 360 degree retention of tube 14 and further inhibits slippage of tube 14 due to the formation of device 1 from, or the coating of device 1 with, a sticky material. Thus, proper positioning of tube 14 is capable of being maintained, while facilitating attachment in an efficient, effective, and ergonomic manner.

From the foregoing and with reference to the various figure drawings, those skilled in the art will appreciate that certain modifications can also be made to the present disclosure without departing from the scope of the same. It is not intended that the above description be limiting but, rather, that the above description be construed merely as an exemplification of the present disclosure. Those skilled in the art will envision other modifications within the scope and spirit of the claims appended hereto.

What is claimed is:

1. A device for securing a tube in position, the device comprising:
    a strip of material defining a first surface and a second, opposed surface, the strip of material including a first end portion, a second end portion, and an intermediate portion;
    a first attachment member disposed on the first surface of the strip of material and positioned adjacent the first end portion;
    a second attachment member disposed on the first surface of the strip of material and positioned adjacent the second end portion; and
    a third attachment member disposed on the second surface of the strip of material and positioned adjacent the intermediate portion,
    wherein the strip of material is configured to wrap around a tube and wherein each of the first, second and third attachment members are configured for releasable engagement with a strap member for securing the tube in position relative to the strap member.

2. The device according to claim 1, wherein the strip of material is formed from a foam.

3. The device according to claim 1, wherein the first surface of the strip of material defines a sticky configuration to facilitate retention of the tube.

4. The device according to claim 1, wherein the strip of material is formed from at least one of a stretchable, flexible, malleable, and elastomeric material.

5. The device according to claim 1, wherein at least one of the first, second, and third attachment members includes an array of hooks configured to releasably engage an array of loops.

6. The device according to claim 1, wherein the strip of material defines an expanded-dimension portion adjacent at least one of the first, second, and third attachment members.

7. A system for securing a tube in position, the system comprising:
    a strap member configured to be secured to a patient, the strap member defining an outwardly-facing surface and including an attachment structure disposed on the outwardly-facing surface; and
    a device, the device including:
        a strip of material defining a first surface and a second, opposed surface, the strip of material including a first end portion, a second end portion, and an intermediate portion;
        a first attachment member disposed on the first surface of the strip of material and positioned adjacent the first end portion;
        a second attachment member disposed on the first surface of the strip of material and positioned adjacent the second end portion; and
        a third attachment member disposed on the second surface of the strip of material and positioned adjacent the intermediate portion,
    wherein the device is configured to wrap around a tube and wherein the first, second, and third attachment members include attachment structures, each of which are configured for releasable engagement with the attachment structure of the strap member for securing the tube in position relative to the strap member.

8. The system according to claim 7, wherein the first surface of the strip of material defines a sticky configuration to facilitate retention of the tube.

9. The system according to claim 7, wherein the strip of material is formed from at least one of a stretchable, flexible, malleable, and elastomeric material.

10. The system according to claim 7, wherein the strap member is formed from a non-stretchable or low stretch material.

11. The system according to claim 7, wherein the first, second, and third attachment members each include an array of hooks and wherein the attachment structure of the strap member includes an array of loops configured to releasably engage the arrays of hooks.

12. The system according to claim 7, wherein the strip of material defines an expanded-dimension portion adjacent at least one of the first, second, and third attachment members to provide greater surface area of engagement between the at least one of the first, second, and third attachment members and the strap member.

13. The system according to claim 7, wherein the tube is configured for positioning adjacent the intermediate portion of the strip of material with the first end portion wrapped about the tube in a first direction and the second end portion wrapped about the tube in a second direction.

14. The system according to claim 7, wherein the first attachment member is configured to engage the strap member on a first side of the tube and wherein the second attachment member is configured to engage the strap member on a second, opposite side of the tube.

15. A method of securing a tube in position, the method comprising:
    providing a strap member;
    providing a device defining a first surface and a second, opposed surface, the device including a first end portion, a second end portion, and an intermediate portion;
    attaching the strap member to a patient;
    releasably engaging the second surface of the device at the intermediate portion thereof to the strap member;
    positioning a tube adjacent the first surface of the device at the intermediate portion thereof;
    wrapping the first end portion of the device about the tube in a first direction;
    releasably engaging the first surface of the device at the first end portion thereof to the strap member;
    wrapping the second end portion of the device about the tube in a second direction; and
    releasably engaging the first surface of the device at the second end portion thereof to the strap member.

16. The method according to claim 15, wherein the device further includes a first attachment member disposed on the first surface adjacent the first end portion, a second attachment member disposed on the first surface adjacent the second end portion, and a third attachment member disposed on the second surface adjacent the intermediate portion, and wherein:
    releasably engaging the second surface of the device at the intermediate portion thereof to the strap member includes releasably engaging the third attachment member to the strap member;
    releasably engaging the first surface of the device at the first end portion thereof to the strap member includes releasably engaging the first attachment member to the strap member; and
    releasably engaging the first surface of the device at the second end portion thereof to the strap member includes releasably engaging the second attachment member to the strap member.

17. The method according to claim 16, wherein at least one of releasably engaging the first attachment member to the strap member, releasably engaging the second attachment member to the strap member, and releasably engaging the third attachment member to the strap member includes releasably engaging a plurality of hooks with a plurality of loops.

18. The method according to claim 15, wherein wrapping the first and second end portions about the tube in opposite directions provides 360 retention of the tube by the device.

* * * * *